US012805983B2

(12) United States Patent
Andersen et al.

(10) Patent No.: US 12,805,983 B2
(45) Date of Patent: Nov. 24, 2026

(54) INTRAORAL SCANNER WITH A HYGIENIC HOUSING

(71) Applicant: 3SHAPE A/S, Copenhagen (DK)

(72) Inventors: Mads Grønlund Andersen, Copenhagen (DK); Serhii Yurko, Copenhagen (DK); Oleksii Borodianskyi, Copenhagen (DK); Anders Larsen, Copenhagen (DK); Oliver Sundberg, Copenhagen (DK); Stina Leghammar, Copenhagen (DK)

(73) Assignee: 3SHAPE A/S, Kobenhavn K (DK)

( * ) Notice: Subject to any disclaimer, the term of this patent is extended or adjusted under 35 U.S.C. 154(b) by 88 days.

(21) Appl. No.: 18/879,664

(22) PCT Filed: Jun. 22, 2023

(86) PCT No.: PCT/EP2023/066976
§ 371 (c)(1),
(2) Date: Dec. 27, 2024

(87) PCT Pub. No.: WO2024/002856
PCT Pub. Date: Jan. 4, 2024

(65) Prior Publication Data

US 2025/0387204 A1 Dec. 25, 2025

(30) Foreign Application Priority Data

Jul. 1, 2022 (EP) .................................... 22182609

(51) Int. Cl.
*A61C 9/00* (2006.01)
*G16H 40/63* (2018.01)

(52) U.S. Cl.
CPC .......... *A61C 9/0053* (2013.01); *G16H 40/63* (2018.01)

(58) Field of Classification Search
CPC ......... A61C 9/0053; A61C 1/16; G16H 40/63
See application file for complete search history.

(56) References Cited

FOREIGN PATENT DOCUMENTS

| | | | | |
|---|---|---|---|---|
| EP | 2442720 B1 | | 8/2016 | |
| WO | 2020053136 A1 | | 3/2020 | |
| WO | WO-2020174048 A1 | * | 9/2020 | ............... A61B 1/24 |

OTHER PUBLICATIONS

International Search Report and Written Opinion of the International Searching Authority (Forms PCT/ISA/237 and PCT/ISA/210) issued on Aug. 18, 2023, by the International Bureau of European Patent Office in corresponding International Application No. PCT/EP2023/066976. (8 pages).

* cited by examiner

*Primary Examiner* — Michael J Carey
(74) *Attorney, Agent, or Firm* — Buchanan Ingersoll & Rooney PC

(57) ABSTRACT

A handheld intraoral scanner configured to acquire intraoral scan data from a three-dimensional dental object during a scanning session including a scan module, a scan tip configured to be connected to the scan module, and a housing that includes a single piece and including a first opening and a second opening opposite to the first opening, wherein one or both of the first opening and second opening are configured to receive at least a part of the scan module.

12 Claims, 13 Drawing Sheets

INTRAORAL SCANNER WITH A HYGIENIC HOUSING

FIELD

The present disclosure relates generally to a hygienic assembly of a handheld intraoral scanner. More specifically, the present disclosure relates to a handheld intraoral scanner including a housing that is made in one piece, and through openings in the housing an insertion and removing of a scan module into and out of the housing is supported.

BACKGROUND

In the field of dentistry, it is of great importance that medical devices meet national and international standards for hygiene to ensure safety of the patient and to ensure safe use of the devices.

This generally implies that medical devices that are in the immediate vicinity of a patient have surfaces that, as much as possible, reduce the risk of contamination.

Surfaces having cavities, even relatively small cavities, such as grooves, may allow fluids from a patient, such as saliva and blood, to reach these cavities, and may allow bacteria to thrive inside them and lead to contamination.

Cavities and grooves in the surface of medical devices will further complicate the process of cleaning the devices, and therefore leads to a further risk of spreading the bacteria to other patients.

Such grooves are usually present in the housing or casing of medical devices, particularly at portions, where different parts of the housing or casing meet.

The disclosure relates to improving hygiene of handheld intraoral scanners and to reduce the risk of contamination of the surface of the housing of handheld intraoral scanners.

Handheld intraoral scanners may need maintenance, cleaning, repairing, or replacements of parts.

The disclosure further relates to a handheld intraoral scanner that allows the removing and insertion of a scan module enclosed by a housing.

Handheld intraoral scanners comprise elements for performing a scan of a dental object. Such elements include a scan probe or tip for reaching the dental object to be scanned inside the oral cavity and an optical lens, wherein an optical axis is defined between the scan tip or probe and the optical lens. The optical axis runs through the scan probe or tip. The optical lens is usually arranged in a scan module, usually enclosed and protected by a housing. Handheld intraoral scanners are usually held by a housing during use. The housing may deform during use, which may have an impact on the optical axis, which leads to a reduction of the scan quality.

The disclosure further relates to a handheld intraoral scanner that reduces the risk of affecting the optical axis during use of the handheld intraoral scanner.

SUMMARY

One aspect of the disclosure is to provide a handheld intraoral scanner that provides for an improvement of the hygiene and reduces the risk of contamination of the surface of the housing of the handheld intraoral scanner.

One further aspect of the disclosure is to provide a handheld intraoral scanner with a hygienic housing that allows for the removing and insertion of a scan module enclosed by a housing. Yet another aspect of the disclosure is to provide a handheld intraoral scanner that reduces the risk of affecting the optical axis during use of the handheld intraoral scanner.

Furthermore, one aspect of the disclosure is to provide an easier assembling of the intraoral scanner when the housing is made of a single piece.

These aspects are provided by the disclosure.

The disclosure relates to a handheld intraoral scanner that may be configured to acquire intraoral scan data from a three-dimensional dental object during a scanning session. The handheld intraoral scanner may comprise a scan module that may be configured to support electronical, optical, and electromechanical parts of the handheld intraoral scanner and may further be configured to slide into a housing thereby allowing for an easier assembly of the handheld intraoral scanner according to an aspect of this disclosure. The scan module may comprise active electronic components such as a processor unit (e.g. a CPU), a drive unit (e.g. an electric motor), etc. The processor unit (such as a central processor unit) may be configured to receive and process the acquired intraoral scan data and generate a virtual 3D model of the three-dimensional dental object. The processor unit may further be configured to display the generated virtual 3D model of the three-dimensional dental object on a display unit. The drive unit (such as an electric motor), may be configured to drive a lens drive that may comprise an optical focus lens and a gear arrangement, and that may be arranged inside the handheld intraoral scanner. The drive unit may be configured to move the optical focus lens back and forth using the lens drive, while intraoral image data is acquired using the optical focus lens of the lens drive, such that intraoral image data may be acquired at different focal points, according to a current position of the optical focus lens. Acquiring intraoral scan data of a three-dimensional dental object at different focal points may allow a for acquiring of intraoral scan data at different layers (i.e. vertical axis) generation of a virtual 3D model of the three-dimensional dental object.

The scan module may further comprise passive electronic components, such as a capacitor, an inductor, a resistors, or electronic wires.

The handheld intraoral scanner may furth comprise a housing that may be configured to at least partly accommodate a part of the scan module, may further be configured to at least partly accommodate at least one of the active electronic components, and may further be configured to be made in a single piece thereby allowing for an improvement of the hygiene of the handheld intraoral scanner according to an aspect of this disclosure. Additionally, the handheld intraoral scanner may comprise a scan tip that may be configured to be at least partly inserted inside the oral cavity of a patient and may further be configured to be connected to the scan tip thereby allowing for a direct connection between the scan tip and the scan module independently of the housing, thereby reducing the risk of affecting an optical axis between the scan module and the scan tip when the housing is deformed, according to an aspect of this disclosure. If the optical axis is affected during a scan session, the scan quality may be reduced, therefore, having an optical axis that is not affected during a scan session may improve the quality of the scan.

The handheld intraoral scanner may further comprise a connection element configured to connect the scan tip to the scan module. Thereby a connection between the scan tip and the scan module is achieved, and the optical axis may therefore not be affected by a deformation of the housing, according to an aspect of this disclosure.

The housing may be configured to enclose at least a part of the scan module and may consist of a single piece or a single part or may be made in a single piece or a single part or may be made as a single piece or a as a single part.

A single piece housing means that the housing has limited number of cavities which dirt can be accumulated over time. Furthermore, a single piece housing means that the housing is molded in such a way that any splices in the housing are avoided or reduced to a minimum. It has been shown that it is difficult to clean properly microscopic cavities which appear in the splices, and therefore, making a housing of a single piece affects the cleaning process of the intraoral scanner in such a way that it becomes more easier to clean.

The feature of the housing consisting of or being made of a single piece, one piece, one part, or a single part may prevent contamination of the surface of the housing of the handheld intraoral scanner, according to an aspect of this disclosure, since the housing has no assembled parts, and therefore has no grooves such as meeting portions.

The housing may comprise a first opening and a second opening opposite to the first opening, wherein one or both of the first opening and second opening may be configured to receive at least a part of the scan module.

The feature of the housing having a first opening and a second opening may allow for a scan module comprising electrical, optical, mechanical, and electromechanical parts to be inserted and removed from the housing, thus allowing for maintenance, replacement or repair of the scan module or parts thereof or thereon, according to an aspect of this disclosure.

The electrical parts may for example be a circuit board, a processor unit, a memory unit, a network unit, a light emitting unit, such as a light diode or projector, and an image sensor. The optical parts may for example be a projector unit, an image sensor, an optical lens, a beam splitter configured to split a ray of light, a pattern generator configured to generate a light pattern when light passes through the pattern generator.

The mechanical parts and electromechanical parts may for example be a lens drive assembly configured to drive an optical lens inside the intraoral scanner and a fan for cooling down the intraoral scanner. The scan module may comprise a support portion configured to support the scan module or the parts of the scan module. The support portion may be a frame.

The scan module may for example include at least a projector unit, at least an image sensor and at least a processor unit. The at least projector unit may include one or more light emitting sources that are configured to emit light at a wavelength range between 10 nm (nanometer) to 1 mm (millimeter). The projector unit may further include none-visible light, such as infrared (e.g. 700 nm to 2000 nm) and/or near-infrared. The projector unit may further comprise UV light, color light (e.g. blue, white, red, yellow and/or green). The image sensor may for example include a monochromatic image sensor or an RGB image sensor. The processor unit may be configured to process the raw image data provided by the image sensor into 2D image data or 3D image data. In other examples, the processor unit may be configured to perform simple image processing or no image processing for being transmitted wirelessly to an external device. In this example, the external device is processing the received image data from the handheld intraoral scanner into 2D image data and/or 3D image data.

The scan module may comprise a support portion, that may for example be a frame. The support portion may be configured to support the parts or the scan module.

The handheld intraoral scanner may further comprise a scan tip that may be configured to be connected to the scan module. The scan tip may include a first opening at a first end and a second opening at a second end opposite to the first end. The scan tip may include a passage defined between the first opening and the second opening, and may be configured to allow light to pass through the passage. The scan tip may be configured to be covered by a scan tip cover that may be configured to be detachably connected to the scan tip. the scan tip cover may be retained on the scan tip by for example a snapping connection, by engaging threads arranged on the outer surface of the scan tip and the inner surface of the scan tip cover, by a friction connection between the scan tip and the scan tip cover, or by screw. The scan tip cover may be configured to prevent fluid such as saliva or blood from a patient from reaching the scan tip. The scan tip cover may comprise an opening that may be covered by a window that may be configured to allow light to pass through. The scan tip cover may be configured to be inserted into the oral cavity of a patient and may be configured to be cleaned inside an autoclave. The scan tip cover may be configured to be detachably connected to a hygienic sleeve covering at least a part of the scan tip cover and the housing and configured to prevent cross contamination between the scan tip cover and the housing by preventing fluids such as saliva and blood to reach across an interface between the scan tip cover and the housing. The scan tip may be configured to be inserted in the oral cavity of a patient and may be configured to allow light from a projector unit inside the intraoral scanner to reach a dental object inside the oral cavity of the patient and may be configured to allow reflected light from the dental object inside the oral cavity to pass towards an image sensor inside the intraoral scanner. The second opening may be arranged at an angle between 45 and 90 degrees relative to the first opening. The second opening may be covered by a window or a transparent sheet configured to allow light to pass through, and configured to prevent fluid, such as saliva or blood from a patient, from entering the passage of the scan tip. The scan tip may further include a mirror at the second end configured to reflect the light at an angle, leading the light from the projector unit inside the intraoral scanner, through the passage of the scan tip, to the dental object inside the oral cavity of a patient, and vice versa. The angle at which the mirror may reflect the light may be between 45 and 90 degrees, which may allow a scan to be performed even at difficult angles. An optical axis within the passage of the scan tip may thus be defined between the first opening of the scan tip and the second opening of the scan tip. The optical axis may further be defined between a projector unit inside the intraoral scanner and a dental object inside the oral cavity of a patient.

The scan tip may be configured to be connected to the scan module. The connection may for example be through engaging threads, a nut, screws, clamps, or an intermediate connection element that may be connected to the scan tip and to the scan module. This allows for a connection between the scan tip and the scan module, thereby allowing for omitting a connection between the scan tip and the housing, and thus allows for reducing the risk of affecting the optical axis between the scan module and the scan tip, according to an aspect of this disclosure.

The scan tip may comprise a threaded portion for engaging a threaded portion on the scan module. The scan tip may comprise holes in the side walls of the scan tip, which may be aligned with holes in the side walls of the scan module or through the side walls of an intermediate connection element connected to the scan module, and by inserting screws through the aligned holes, a direct connection may further be achieved between the scan tip and the scan module. Thereby allowing for a reduced risk of affecting the optical axis, according to an aspect of this disclosure.

The housing may comprise an open channel defined between the first opening and the second opening, and wherein the channel may be configured to accommodate at least a part of the scan module.

The feature of the open channel may allow for a scan module to be inserted and removed from any of the openings, and allows for a part of the scan module to be inserted and another part of the scan module to protrude out of the housing.

At least a part of the scan module may be configured to slide into either the first opening or the second opening of the housing. The sliding may be supported by protruding parts of the scan module that may engage with guides arranged on an inner surface of the housing, or vice versa. The sliding may be supported by indentations in the scan module that may engage with protruding parts arranged on an inner surface of the housing. The sliding may further be supported by the housing or channel arranged on an inner surface of the housing in that at least a section of the housing or the channel inside the housing having a larger cross-sectional area than at least a section of the scan module. The sliding of the scan module allows for an easy mounting of the scan module into the housing.

The open channel of the housing may be configured to support a sliding motion of the scan module.

The feature of the scan module sliding into the housing may reduce the complexity of assembling the handheld intraoral scanner.

At least a part of the scan module may be configured to be inserted into either the first opening and the second opening of the housing, and when the scan module is inserted into one of the first opening or second opening of the housing, at least a part of the scan module may be configured to protrude out of the first opening of the housing.

The protruding of the at least part of the scan module out of the first opening of the housing may allow the scan module to be connected to a connection element or to another part of the handheld intraoral scanner. The feature of having a connection element arranged on the protruding part of the scan module may allow the scan tip to be connected directly to the scan module and not to the housing, thereby reducing the risk of affecting the optical axis if the housing is deformed, according to an aspect of the disclosure. The feature of reducing the risk of affecting the optical axis by a deformed housing may also be achieved by connecting the protruding part of the scan module directly to the scan tip without a connection element, for example by engaging a threaded portion arranged on the scan tip with a threaded portion arranged on the protruding part of the scan module. The connection element may be formed as a ring or a nut, such that the scan module may be connected to a part of the ring or nut, and the scan tip may be connected to another part of the ring or nut. The parts on the connection element may comprise threads or holes in the side wall of the connection element configured to receive a screw, for connecting the scan tip and the scan module to the connection element.

The connection element may be connected to the scan module by arranging the connection element on the support portion and retaining the position of the connection element by applying a retainer element, for example a locking ring.

The housing may comprise a flange at the first opening that may be configured to abut an abutment of the scan module. The flange may be a part of an inner wall of the housing or the channel that may be arranged in about 90 degrees angle relative to a longitudinal direction of the housing or of the channel and may be arranged at the edge of the first opening of the housing. The flange may be configured to stop scan module when the scan module slides through the channel. The stopping may occur when an abutment of the scan module such as a protrusion reaches the flange and abuts against it.

The flange may be configured to prevent at least a part of the scan module from moving out of the first opening when a part of the scan module is received by the housing.

The scan module may comprise an abutment that may be configured to abut the flange of the housing.

The feature of a flange at the first opening of the housing and an abutment of the scan module may allow for the removing and insertion of a scan module enclosed by a housing, according to an aspect of the disclosure.

The flange may prevent the scan module from sliding out of the first opening, after the scan module has been inserted into the housing through the second opening. The flange may further allow the scan module to be fixated inside the housing, since a connection element and a retainer may be arranged on a part of the scan module protruding out of the first opening to one side of the flange, and pressing the abutment of the scan module to the other side of the flange against the flange. Thereby is achieved that fastening means, such as screws or clips, that penetrate fully or partly the housing are avoided for easier disassembling. The fastening means may further pose a risk of contamination in the surroundings of the holes or cavity for the fastening means. Furthermore, the use of a connection element as described above, allows for an assembly where glue is avoided, thereby allowing a releasable attachment between the scan module and the housing.

The scan module may comprise a support portion that may be arranged at a first end of the scan module and may be configured to be connected to a connection element or to the scan tip. The support portion may be a portion of the scan module or may be a frame that supports the scan module or parts of the scan module. The frame may be a plastic frame or a metal frame. The support portion may comprise a channel that may be configured to allow light to pass through. The connection element may for example be an element that is configured to be arranged on the support portion of the scan module and may be configured to connect the scan module to the scan tip, and may be formed as a ring or a nut.

The frame may be a frame housing.

The scan module may comprise a frame housing that may accommodate the at least one active electronic components. The frame housing may include a support portion that may be configured to support the frame housing to the housing. The support portion may be arranged outside the housing and the remaining of the frame housing may be arranged within the housing. The connection element may be removably fixated to the support portion and an outer surface of the housing.

The connection element may be removably fixated to the support portion and a flange of the outer surface of the housing.

The support portion may reduce the complexity of connecting the scan module to other parts such as a connection element or the scan tip according to an aspect of the disclosure, and may allow light to pass to and from the optical parts of the handheld intraoral scanner.

The handheld intraoral scanner may further comprise a connection element that may be configured to connect the scan tip to the scan module or the scan tip to the support portion. The connection element may allow a direct connection between the scan module and the scan tip, and may thereby reduce the risk of affecting the optical axis according to an aspect of the disclosure. The connection element may be arranged on the scan module. The connection element may be arranged on the support portion of the scan module. The connection element may be arranged on a part of the scan module or the support portion of the scan module that protrudes out of the first hole of the housing. The connection element may be a ring. The connection element may comprise a groove in an opening through the connection element. The groove may be configured to accommodate or to abut a protrusion of the scan module or of the support portion of the scan module. The connection element may comprise an insertion hole going through the side wall of the connection element and to the groove, and configured to receive an insertion element, which may be a screw, and configured to be inserted into the insertion hole and configured to abut the protrusion of the support portion of the scan module when accommodate inside the groove, which may prevent the connection element from rotating, and thereby, may reduce the risk of affecting the optical axis according to an aspect of the disclosure. The connection element may comprise one or more holes in the outer wall of the connection element that may be configured to receive a screw in each hole. The connection element may be configured to be arranged on the part of the scan module or of the support portion of the scan module that protrudes out of the first opening and may be configured to be arranged to abut a flange of the housing arranged at the first opening and may be configured to be connected to the scan tip. The connection may occur by for example aligning holes in the sidewall of the scan tip with the holes in the sidewall of the connection element and inserting a screw that goes through the hole in the sidewall of the scan tip and through the respective hole in the sidewall of the connection element. The connection element may be fixated or retained into position and configured to apply a pressure on the scan module or support portion of the scan module and the flange, by abutting and tightening a retainer element against the connection element. The retainer element may for example be a retainer ring, a locking ring, or a nut. The retainer ring, the locking ring, and the nut may be tightened by screwing them onto a threaded portion of the scan module or the support portion of the scan module. The connection element may further be a ring that comprises a threaded portion on the inner surface that is configured to engage a threaded portion on the scan module or on the support portion of the scan module.

The protrusion of the scan module may be arranged on an outer surface of the support portion.

The housing may be manufactured in one single piece such that the outer surface of the housing does not comprise any assembled parts. The outer surface of the housing may therefore not comprise any meeting surfaces. Thus, the outer surface of the housing may not be composed of an assembly, but may be composed of one single integral piece. The inner surface of the housing may comprise assembly interfaces, such as grooves, clamps, protruding elements, threads, etc., that may be configured to connect the scan module and/or a power module, such as a battery, a battery module, a power cable, a power interface, or a wired power interface.

A housing that is e.g. comprised of two shell-parts, is considered an assembly, since the two shell-parts are assembled into forming the housing. The present disclosure discloses a housing that is not comprised of two or more parts, but is formed as one integral piece. This may be achieved by e.g. injection molding the housing in one single piece, and thus no assembling is needed to manufacture the housing.

The scan tip may comprise one or more holes, the connection element may comprise one or more holes, the one or more holes of the scan tip and the one or more holes of the connection element may be configured to be aligned when the scan tip is connected to the scan module, and each of the one or more holes of the scan tip and the one or more holes of the connection element may be configured to receive a screw when the scan tip is connected to the connection element. The connection between the scan tip and the connection element may allow a direct connection between the scan module and the scan tip, and may thereby reduce the risk of affecting the optical axis according to an aspect of the disclosure.

The connection element may be configured to be arranged on the support portion of the scan module. The connection element may be configured to be arranged on the part of the scan module that protrudes out of the first opening. Arranging the connection element on the support portion or the part of the scan module that protrudes out of the first opening may reduce the complexity of assembling the handheld intraoral scanner.

A surface of the connection element may comprise a groove that may be configured to accommodate a protrusion of the scan module or the support portion of the scan module. The scan module or the support portion of the scan module may comprise a protrusion that may be configured to accommodate the groove in the surface of the connection element. The feature of having a groove in the connection element accommodating a protrusion in the support portion may prevent a rotation of the connection element thereby reducing the risk of affecting the optical axis according to an aspect of the disclosure.

The protrusion of the scan module or the support portion may be configured to prevent a rotation of the connection element around an axis through the longitudinal direction of the connection element when the protrusion is accommodated by the groove of the connection element. The protrusion of the scan module may prevent the connection element from rotating, and therefore may prevent movement of the connection between the scan tip and the scan module, and thereby may reduce the risk of affecting the optical axis, and thereby may improve the quality of the scan.

The connection element may be a ring that may be configured to connect the scan module to the scan tip. The connection element may be circular or may resemble a different shape. The connection element may be a closed ring or may not be a closed ring that may contain two ends that do not meet, thereby only partly enclosing a gap or opening through the ring.

Forming the connection element as a ring may reduce the complexity of having a connection element connecting the scan tip to the scan module. The ring may simply be inserted onto the scan module. This feature may allow for a simple arrangement of the connection element on the scan module or on the support portion of the scan module.

The connection element may further comprise a retainer element, that may be configured to be arranged on the scan module or on the support portion of the scan module and may be configured to retain a position of the connection element or may be configured to prevent a movement of the connection element. The retainer may be a retainer ring, a locking ring, or a nut that may have a threaded portion arranged on an inner surface. The threaded portion of the retainer may be configured to engage a threaded portion of the scan module. The retainer may be screwed into position on the scan module after the connection element has been arranged on the scan module or on the support portion of the scan module, thereby locking the connection element into position between the scan module and the retainer. When the retainer element abuts the connection element, the retainer may be tightened and may press the connection element towards the flange of the housing, thereby pressing the scan module or the support portion of the scan module against the flange, thereby providing a fixation of the connection element and the scan module and providing a rigid connection between the connection element and the scan module.

The feature of having a retainer element may prevent the scan module to move away from its position which may affect the integrity of the scanner and the retainer element thereby reduces the risk of affecting the optical axis according to an aspect of the disclosure.

The retainer element may be a retainer ring or a nut. The retainer element being a ring or a nut allows for a less complex assembly of the handheld intraoral scanner.

A sealing element may be provided between the scan tip and the housing and may be configured to prevent fluids from reaching an interface or entering a gap between the scan tip and the scan module. The sealing element may prevent fluids from a patient, such as saliva or blood, to reach an interface or a gap between the scan tip and the housing, thereby reducing the risk of contamination, and thereby improving the hygiene of the handheld intraoral scanner, according to an aspect of the disclosure.

The sealing element may for example be a gasket, an O-ring, or a polymer sheet such as rubber or plastic. The sealing element may be arranged such that it forms a water-tight enclosure around a part of the housing and around a part of the scan tip at the interface where the housing and scan tip meet. The sealing may for example be arranged on the support portion of the scan tip before or after the connection element or before or after the retainer element. The sealing element may be made of a flexible material such as a polymer material such as rubber.

The sealing element may be a gasket.

The scan module may comprise an optical lens, the scan tip may comprise a passage that may be configured to allow light to pass through at least a part of the passage, and wherein when the scan tip is connected to the scan module, an optical axis may be defined between the optical lens and a cross-section of at least a part of the passage.

The feature of an having an optical axis defined between the optical lens and a cross-section of at least a part of the passage allows light to pass unhindered between the optical lens inside the intraoral scanner and the passage through the scan tip at a part (connection element) connecting the scan tip and the scan module.

The scan module may comprise an optical lens, the scan tip may comprise a passage that may be configured to allow light to pass through at least a part of the passage, and wherein when the scan tip is connected to the scan module, an optical axis between the optical lens and the scan tip may pass through a cross-section of the connection element.

The feature of an optical axis passing through a cross-section of the connection element may allow light to pass unhindered between the optical lens inside the intraoral scanner and the passage through the scan tip at a part (connection element) connecting the scan tip and the scan module.

The scan tip may be configured to be aligned with the scan module.

The scan tip may be configured to be aligned with the scan module by connecting the scan tip to an outer surface of the ring and connecting the scan module to an inner surface of the ring, or vice versa.

The feature of having the scan tip being aligned with the scan module allows the optical axis to be connected directly to the scan module and not dependent on the housing. Thus, the effect of a deformed housing on the optical axis may thus be reduced, according to an aspect of the disclosure.

The alignment may occur by a rigid and direct connection between the scan tip and the scan module. The rigid and direct connection between the scan tip and the scan module may be by any of the connection elements mentioned in the previous sections. The rigid and direct connection may further occur by a connection element between the scan tip and the scan module. The connection element may be a ring or a nut connected to the scan tip and to the scan module, as described in the previous sections.

The scan module may be configured to be aligned with the connection element, and wherein the scan tip may be configured to be aligned with the connection element. The feature of having the scan module and the scan tip being aligned with the connection element, allows the optical axis to be connected directly to the scan module and not dependent on the housing. Thus, the effect of a deformed housing on the optical axis may thus be reduced, according to an aspect of the disclosure.

The alignment may occur by a rigid and fixed direct connection between the scan tip and the connection element, and between the connection element and the scan module. The connection element may be a ring or a nut connected to the scan tip and to the scan module, as described in the previous sections.

The housing may comprise a user interface. The user interface may be a part of the housing. The user interface may be manufactured as one part or a single part or a single piece or a single part with the housing. The user interface may be made with the housing by casting or molding such as injection molding. The indication of a position of a user interface may be a visual or haptic marking on the surface of the housing. The user interface may resemble buttons. The user interface may be buttons. The user interface may be formed as one or more elevated surface or surfaces of the housing. The user interface may be made as areas or one or more surface or surfaces of thinner material than the surrounding surface of the housing. The user interface may be made of a more flexible material than the rest of the housing.

The housing may comprise an indication of a position of a user interface. The user interface may be a part of the housing. The user interface may be manufactured as one part or a single part or a single piece or a single part with the housing. The user interface may be made with the housing by casting or molding such as injection molding. The indication of a position of a user interface may be a visual or haptic marking on the surface of the housing. The user interface may resemble buttons. The user interface may be buttons. The user interface may be formed as one or more elevated surface or surfaces of the housing. The user interface may be made as areas or one or more surface or surfaces of thinner material than the surrounding surface of the housing. The user interface may be made of a more flexible material than the rest of the housing.

The feature of a user interface or an indication of a position of a user interface comprised in the housing may allow for improving the hygiene of the handheld intraoral scanner, according to an aspect of the disclosure, since the interface, which may comprise buttons, or the indication of a position of a user interface, which may comprise a marking or an uneven surface of the housing, is a part of the housing, and thereby made in one piece with the housing, and thereby may not contain grooves, gaps, or space for fluids from a patient, such as saliva or blood, to get into. The user interface or the indication of a position of a user interface may comprise one or more buttons. The buttons may be part of the housing. The buttons may be made in one cast or mold with the rest of the housing. The buttons may be visual or haptic markings. The buttons may be elevated areas on the surface of the housing. The buttons may be made of thinner material than the surrounding surface of the housing. The feature of a user interface or an indication of a position of a user interface comprised in the housing may allow for improving the hygiene of the handheld intraoral scanner, according to an aspect of the disclosure, since the interface, which may comprise buttons, or the indication of a position of a user interface, which may comprise a marking or an uneven surface of the housing, is a part of the housing, and thereby made in one piece with the housing, and thereby may not contain grooves, gaps, or space for fluids from a patient, such as saliva or blood, to get into.

The scan module may be configured to be inserted into the first opening of the housing, and a part of the scan module may be configured to protrude out of the first opening of the housing. This may allow one end of the scan module to be inserted into one opening, and allow another end of the scan module to protrude through the same. This may allow to reduce the complexity of the assembly of the handheld intraoral scanner, according to an aspect of the disclosure.

DESCRIPTION OF THE DRAWINGS

Aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

DETAILED DESCRIPTION

Figure 1:
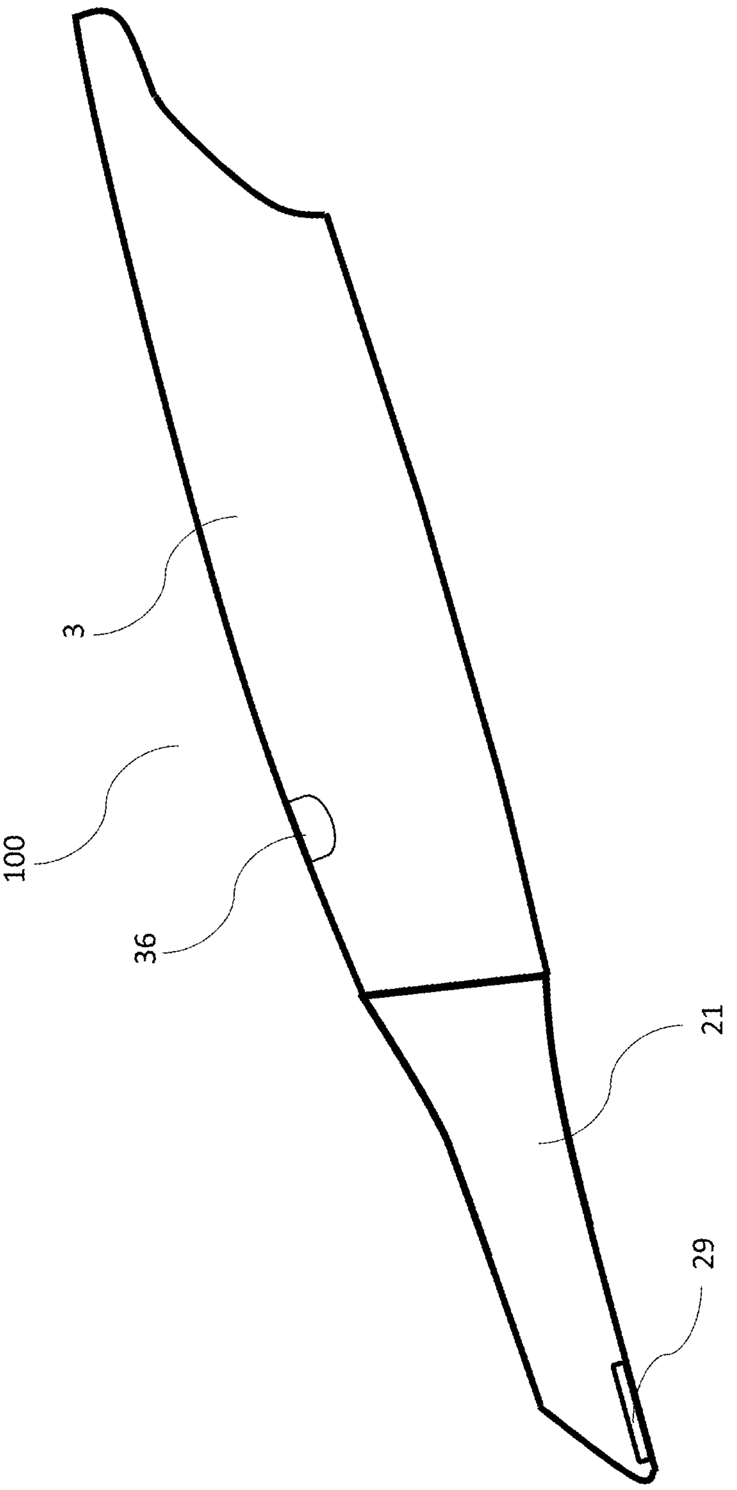
FIG. 1 is a schematic illustration of a handheld intraoral scanner according to an embodiment of the disclosure.

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the devices, systems, mediums, programs and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof. The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout this disclosure. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

A scanning for providing intra-oral scan data may be performed by a dental scanning system that may include an intraoral scanning device such as the TRIOS® series scanners from 3Shape A/S or a laboratory-based scanner such as the E-SERIES™ scanners from 3Shape A/S. The dental scanning system may include a wireless capability as provided by a wireless network unit. The scanning device may employ a scanning principle such as triangulation-based scanning, confocal scanning, focus scanning, ultrasound scanning, x-ray scanning, stereo vision, structure from motion, optical coherent tomography OCT, or any other scanning principle. In an embodiment, the scanning device is capable of obtaining surface information by operated by projecting a pattern and translating a focus plane along an optical axis of the scanning device and capturing a plurality of 2D images at different focus plane positions such that each series of captured 2D images corresponding to each focus plane forms a stack of 2D images. The acquired 2D images are also referred to herein as raw 2D images, wherein raw in this context means that the images have not been subject to image processing. The focus plane position is preferably shifted along the optical axis of the scanning system, such that 2D images captured at a number of focus plane positions along the optical axis form said stack of 2D images (also referred to herein as a sub-scan) for a given view of the object, i.e. for a given arrangement of the scanning system relative to the object. After moving the scanning device relative to the object or imaging the object at a different view, a new stack of 2D images for that view may be captured. The focus plane position may be varied by means of at least one focus element, e.g., a moving focus lens. The scanning device is generally moved and angled relative to the dentition during a scanning session, such that at least some sets of sub-scans overlap at least partially, in order to enable reconstruction of the digital dental 3D model by stitching overlapping sub scans together in real-time and display the progress of the virtual 3D model on a display as a feedback to the user. The result of stitching is the digital 3D representation of a surface larger than that which can be captured by a single sub-scan, i.e. which is larger than the field of view of the 3D scanning device. Stitching, also known as registration and fusion, works by identifying overlapping regions of 3D surface in various sub-scans and transforming sub-scans to a common coordinate system such that the overlapping regions match, finally yielding the digital 3D model. An Iterative Closest Point (ICP) algorithm may be used for this purpose. Another example of a scanning device is a triangulation scanner, where a time varying pattern is projected onto the dental object and a sequence of images of the different pattern configurations are acquired by one or more cameras located at an angle relative to the projector unit.

Color texture of the dental object may be acquired by illuminating the object using different monochromatic colors such as individual red, green and blue colors or my illuminating the object using multichromatic light such as white light. A 2D image may be acquired during a flash of white light.

Generally the process of obtaining surface information in real time of a dental object to be scanned requires the scanning device to illuminate the surface and acquire high number of 2D images. Typically a high speed camera is used with a framerate of 300-2000 2D frames pr second dependent on the technology and 2D image resolution. The high amount of image data needed to be handled by the scanning device to eighter directly forward the raw image data stream to an external processing device or performing some image processing before transmitting the data to an external device or display. This process requires that multiple electronic components inside the scanner is operating with a high workload thus requiring a high demand of current.

The scanning device comprises one or more light projectors configured to generate an illumination pattern to be projected on a three-dimensional dental object during a scanning session. The light projector(s) preferably comprises a light source, a mask having a spatial pattern, and one or more lenses such as collimation lenses or projection lenses. The light source may be configured to generate light of a single wavelength or a combination of wavelengths (mono- or polychromatic). The combination of wavelengths may be produced by using a light source configured to produce light (such as white light) comprising different wavelengths. Alternatively, the light projector(s) may comprise multiple light sources such as LEDs individually producing light of different wavelengths (such as red, green, and blue) that may be combined to form light comprising the different wavelengths. Thus, the light produced by the light source may be defined by a wavelength defining a specific color, or a range of different wavelengths defining a combination of colors such as white light. In an embodiment, the scanning device comprises a light source configured for exciting fluorescent material of the teeth to obtain fluorescence data from the dental object. Such a light source may be configured to produce a narrow range of wavelengths. In another embodiment, the light from the light source is infrared (IR) light, which is capable of penetrating dental tissue. The light projector(s) may be DLP projectors using a micro mirror array for generating a time varying pattern, or a diffractive optical element (DOF), or back-lit mask projectors, wherein the light source is placed behind a mask having a spatial pattern, whereby the light projected on the surface of the dental object is patterned. The back-lit mask projector may comprise a collimation lens for collimating the light from the light source, said collimation lens being placed between the light source and the mask. The mask may have a checkerboard pattern, such that the generated illumination pattern is a checkerboard pattern. Alternatively, the mask may feature other patterns such as lines or dots, etc.

The scanning device preferably further comprises optical components for directing the light from the light source to the surface of the dental object. The specific arrangement of the optical components depends on whether the scanning device is a focus scanning apparatus, a scanning device using triangulation, or any other type of scanning device. A focus scanning apparatus is further described in EP 2 442 720 B1 by the same applicant, which is incorporated herein in its entirety.

The light reflected from the dental object in response to the illumination of the dental object is directed, using optical components of the scanning device, towards the image sensor(s). The image sensor(s) are configured to generate a plurality of images based on the incoming light received from the illuminated dental object. The image sensor may be a high-speed image sensor such as an image sensor configured for acquiring images with exposures of less than 1/1000 second or frame rates in excess of 250 frames pr. Second (fps). As an example, the image sensor may be a rolling shutter (CCD) or global shutter sensor (CMOS). The image sensor(s) may be a monochrome sensor including a color filter array such as a Bayer filter and/or additional filters that may be configured to substantially remove one or more color components from the reflected light and retain only the other non-removed components prior to conversion of the reflected light into an electrical signal. For example, such additional filters may be used to remove a certain part of a white light spectrum, such as a blue component, and retain only red and green components from a signal generated in response to exciting fluorescent material of the teeth.

The network unit may be configured to connect the dental scanning system to a network comprising a plurality of network elements including at least one network element configured to receive the processed data. The network unit may include a wireless network unit or a wired network unit. The wireless network unit is configured to wirelessly connect the dental scanning system to the network comprising the plurality of network elements including the at least one network element configured to receive the processed data. The wired network unit is configured to establish a wired connection between the dental scanning system and the network comprising the plurality of network elements including the at least one network element configured to receive the processed data.

The dental scanning system preferably further comprises a processor configured to generate scan data (intra-oral scan data) by processing the two-dimensional (2D) images acquired by the scanning device. The processor may be part of the scanning device. As an example, the processor may comprise a Field-programmable gate array (FPGA) and/or an Advanced RISC Machines (ARM) processor located on the scanning device. The scan data comprises information relating to the three-dimensional dental object. The scan data may comprise any of: 2D images, 3D point clouds, depth data, texture data, intensity data, color data, and/or combinations thereof. As an example, the scan data may comprise one or more point clouds, wherein each point cloud comprises a set of 3D points describing the three-dimensional dental object. As another example, the scan data may comprise images, each image comprising image data e.g. described by image coordinates and a timestamp (x, y, t), wherein depth information can be inferred from the timestamp. The image sensor(s) of the scanning device may acquire a plurality of raw 2D images of the dental object in response to illuminating said object using the one or more light projectors. The plurality of raw 2D images may also be referred to herein as a stack of 2D images. The 2D images may subsequently be provided as input to the processor, which processes the 2D images to generate scan data. The processing of the 2D images may comprise the step of determining which part of each of the 2D images are in focus in order to deduce/generate depth information from the images. The depth information may be used to generate 3D point clouds comprising a set of 3D points in space, e.g., described by cartesian coordinates (x, y, z). The 3D point clouds may be generated by the processor or by another processor unit. Each 2D/3D point may furthermore comprise a timestamp that indicates when the 2D/3D point was recorded, i.e., from which image in the stack of 2D images the point originates. The timestamp is correlated with the z-coordinate of the 3D points, i.e., the z-coordinate may be inferred from the timestamp. Accordingly, the output of the processor is the scan data, and the scan data may comprise Image data and/or depth data, e.g. described by image coordinates and a timestamp (x, y, t) or alternatively described as (x, y, z). The scanning device may be configured to transmit other types of data in addition to the scan data. Examples of data include 3D information, texture information such as infra-red (IR) images, fluorescence images, reflectance color images, x-ray images, and/or combinations thereof. FIG. 1 shows a schematic illustration of a handheld intraoral scanner 100 according to a preferred embodiment. The housing 3 is shown with a scan tip cover 21 and a cover window 29 configured to allow light to pass through the scan tip cover 21. The housing 3 is shown comprising a user interface 36 on a top surface of the housing 3. The user interface 36 is illustrated as a button, but may in other embodiments be a part of the housing 3. The user interface 36 may be a visual or haptic indication of a position of a user interface. The user interface 36 may also be an area of the surface of the housing 3 having a smaller thickness than the surrounding surface of the housing 3 making that particular surface more flexible than the surrounding surface of the housing 3.

Figure 2:
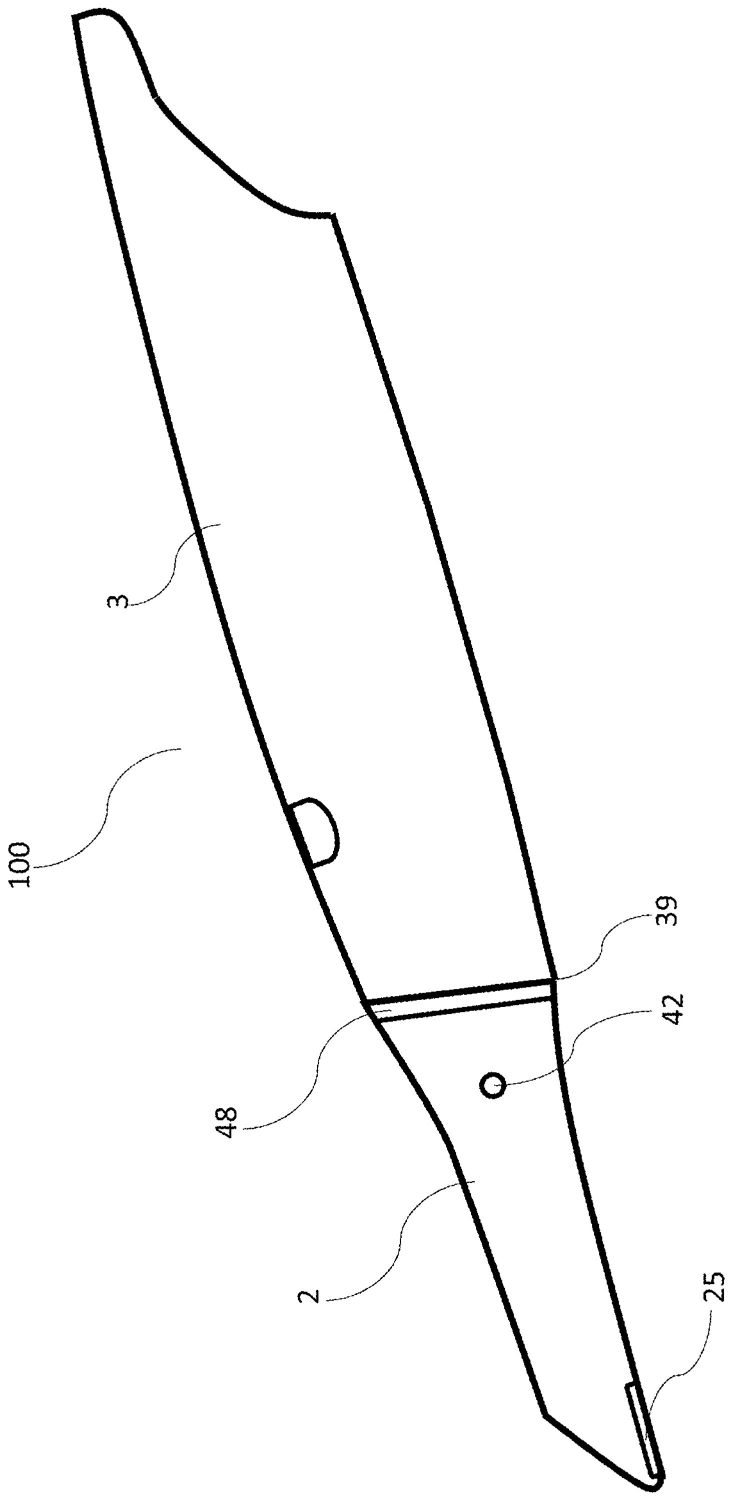
FIG. 2 is a schematic illustration of a handheld intraoral scanner according to an embodiment of the disclosure where the scan tip cover is removed and the scan tip uncovered.

FIG. 2 shows a schematic illustration of the handheld intraoral scanner 100 of FIG. 1, where the scan tip cover 21 (shown in FIG. 1) is removed, disclosing a scan tip 2. The scan tip 2 is shown having a screw 42 going through a hole in a side wall of the scan tip 2. The top of the screw may also function as a retainer for retaining the scan tip cover 21 (FIG. 1) into position when covering the scan tip 2. A sealing element 48 (such as a gasket) is shown arranged between the scan tip 2 and the housing 3.

Figure 3:
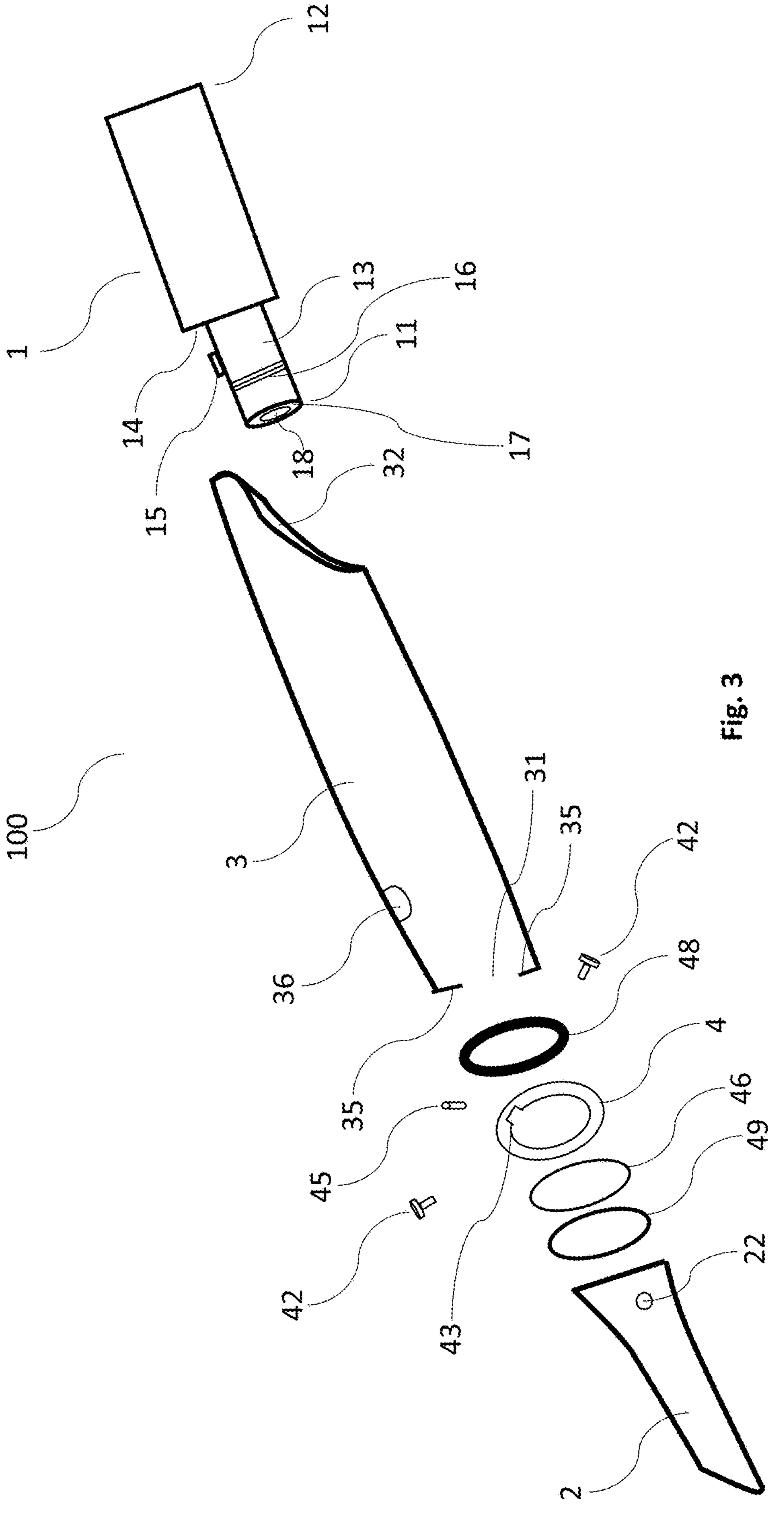
FIG. 3 is a schematic illustration of an exploded view of the handheld intraoral scanner according to an embodiment of the disclosure.

FIG. 3 shows a schematic illustration of an exploded view of the handheld intraoral scanner 100. The scan module 1 is shown as an elongate part having a first end 11 and a second end 12. The scan module 1 is shown comprising a support portion 13, which may be a frame, whereon parts of the scan module 1 are arranged. The support portion 13 may be made of a polymer material such as plastic. A part of the support portion 13 of the scan module 1 is shown extending from an abutment 14 of the scan module 1, and shown as having a circular cross-section. The support portion 13 of the scan module 1 may be an integrated part of the scan module 1 and thereby casted or molded together with the rest of the scan module 1, or may be a separate part that is connected to the scan module 1. The scan module 1 comprises electronic parts such as circuit boards, a computing processor, and a memory. The scan module 1 comprises electromechanical systems such as a drive for moving a focus lens and a fan for cooling the handheld intraoral scanner 100. The scan module 1 comprises optical parts such as lenses, a beam splitter, a pattern generator, and a light emitter. The support portion 13 of the scan module 1 comprises an opening 17 and a channel 18 for allowing light to pass from a light emitter inside the scan module 1 to a dental object inside the oral cavity, and light reflecting from the dental object and to an image sensor inside the scan module 1. The support portion 13 comprises a threaded portion 16 on the outer surface for engagement with a threaded portion 47 (shown in FIG. 9) of a locking ring 46. The housing 3 is further shown with the user interface 36 and the first opening 31 and the second opening 32. The scan tip 2 is shown having a hole 22 in the side wall, for receiving a screw 42 and connecting the scan tip 2 to a connection element 4. The connection element 4 is shown as a ring having a hole 41 (shown in FIGS. 8, 10, 11) in the side wall. The connection element 4 further comprises a groove 43 in the inner surface for abutting a protrusion 15 protruding from the support portion 13 of the scan module 1. The connection element 4 further comprises an insertion hole 44 (shown in FIGS. 8 and 11) through the side wall of the connection element 4 having an opening at the groove 43, for receiving an insertion element 45, which may be a screw for fixating the connection element 4 to the support portion 13 of the scan module 1 and preventing the connection element 4 from rotating. A retainer element 46 is further shown as a locking ring, comprising a threaded portion 47 (shown in FIG. 9) on an inner surface for engagement with the threaded portion 16 of the support portion 13 of the scan module 1 and for tightening the retainer element 46 against the connection element 4, thereby connecting the connection element 4 to the support portion 13 of the scan module 1, and preventing the connection element 4 from movement, and for pressing the support portion 13 of the scan module 1 against a flange 35 of the housing 3 arranged at the first opening 31 of the housing 3, thereby preventing the scan module 1 from sliding out of the housing 3 through the second opening 32 of the housing 3. A sealing element 48, shown as an O-ring, is arranged at an interface 39 (shown in FIG. 2) between the connection element 4 and the first opening 31 of the housing 3. A protection element 49 is further shown arranged between the scan tip 2 and the retainer element 46 configured to protect the scan tip 2 from physical damage when being in contact with the retainer element 46 or the connection element 4.

The scan module 1 is shown to be configured to be inserted into the channel 34 of the housing 3 through the second opening 32 and a part of the support portion 13 being configured to protrude out of the first opening 31.

In an embodiment where the scan module 1 may be inserted into the housing 3 through the first opening 31 and where the flange 35 does not form a complete circle along the first opening 31, the scan module 1 may be inserted through the first opening 31 of the housing 3 by rotating the abutment 14 (shown in FIG. 7) of the scan module 1 at an angle such as to not abut the flange 35 of the housing 3 while the scan module 1 is inserted into the housing 3, and rotated back again after being inserted into the first opening 31, such that the abutment 14 of the scan module 1 abuts the flange 35 while a portion of the scan module 1 is inside the housing 3 while at least a part of the support portion 13 of the scan module 1 protrudes out of the first opening 31. In this way, the scan module 1 will be retained inside the housing 3, when the connection element 4 and the retainer element 46 are arranged on the support portion 13 of the scan module 1. This allows for the scan module 1 to further be inserted through the first opening 31 of the housing 3 and not through the second opening 32 only. Thereby is achieved that fastening means, such as screws or clips, that penetrate fully or partly the housing 3 are avoided for easier disassembling. The fastening means do further pose a risk of contamination in the surroundings of the holes or cavity for the fastening means. Furthermore, the use of a connection element 4 as described above, allows for an assembly where glue is avoided, thereby allowing a releasable attachment between the scan module 1 and the housing 3.

The housing 3 is manufactured in one single piece such that the outer surface of the housing 3 does not comprise any assembled parts. The outer surface of the housing 3 does therefore not comprise any meeting surfaces. Thus, the outer surface of the housing 3 is not composed of an assembly, but is composed of one single integral piece. The inner surface of the housing 3 does comprise assembly interfaces, such as grooves, clamps, protruding elements, threads, etc., that are configured to connect the scan module 1 and/or a power module, such as a battery, a battery module, a power cable, a power interface, or a wired power interface. The scan module 1 comprises active electronic components such as a processor unit (e.g. a CPU), a drive unit (e.g. an electric motor), etc. The processor unit (such as a central processor unit) is configured to receive and process the acquired intraoral scan data and generate a virtual 3D model of the three-dimensional dental object. The processor unit is further configured to display the generated a virtual 3D model of the three-dimensional dental object on a display unit. The drive unit (such as an electric motor), is configured to drive a lens drive that does comprise an optical focus lens and a gear arrangement, and is arranged inside the handheld intraoral scanner 100. The drive unit is configured to move the optical focus lens back and forth using the lens drive, while intraoral image data is acquired using the optical focus lens of the lens drive, such that intraoral image data is acquired at different focal points, according to a current position of the optical focus lens. Acquiring intraoral scan data of a three-dimensional dental object at different focal points allows for acquiring of intraoral scan data at different layers (i.e. vertical axis) generation of a virtual 3D model of the three-dimensional dental object.

The scan module 1 further comprises passive electronic components, such as a capacitor, an inductor, a resistors, or electronic wires.

The housing 3 of the handheld intraoral scanner 100 is configured to at least partly accommodate a part of the scan module 1. The housing 3 is further configured to at least partly accommodate at least one of the active electronic components, and is further configured to be made in a single piece thereby allowing for an improvement of the hygiene of the handheld intraoral scanner 100 according to an aspect of this disclosure.

Figure 4B:
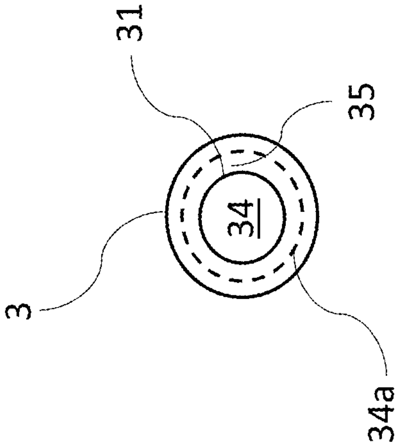
FIG. 4B is a schematic illustration of a front view of the illustration in FIG. 4A.
Figure 4A:
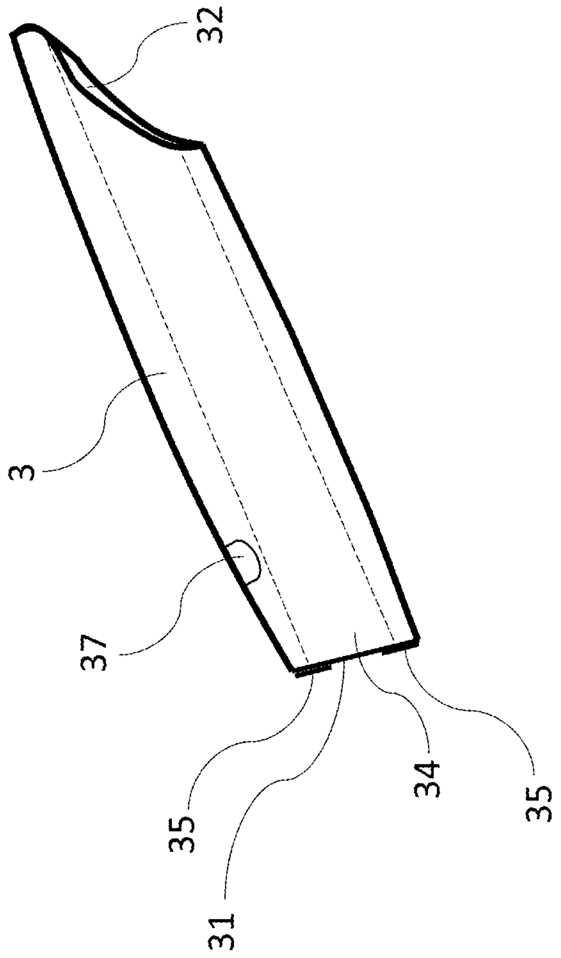
FIG. 4A is a schematic illustration of a perspective view of the housing of the handheld intraoral scanner according to an embodiment of the disclosure.

FIG. 4A shows a schematic illustration of the housing 3 indicating the first opening 31, the second opening 32, the indication of a position 37 of a user interface, and the channel 34 (indicated by dotted lines) defined between the first opening 31 and the second opening 32. The flange 35 is shown arranged at the first opening 31, indicated as a circular wall along the circumference of the first opening 31 extending perpendicular relative to the longitudinal direction of the housing 3 and having a substantially 90 degrees angle relative to the connecting side wall of the housing 3. The flange is a part of the housing and is formed, for example by molding or injection molding, together with the housing. The flange 35 is configured to abut an abutment 14 (shown in FIG. 7) of the support portion 13 (shown in FIGS. 3, 7, 12, 13) of the scan module 1 (shown in FIG. 3) when the scan module 1 is inserted into the channel 34 of the housing 3 thereby preventing the scan module 1 from sliding entirely out of the first opening 31.

FIG. 4B shows a schematic illustration of front view of the housing shown in FIG. 4A. The housing 3 is shown comprising the channel 34 and the flange 35 protruding from the side wall of the housing 3 along the entire circumference of the first end 31 of the housing 3 in a 90 degrees angle relative to the sidewall of the housing 3. The channel 34 of the housing is indicated (by a dotted circle) as extending behind the flange 35 into the housing 3.

Figure 5:
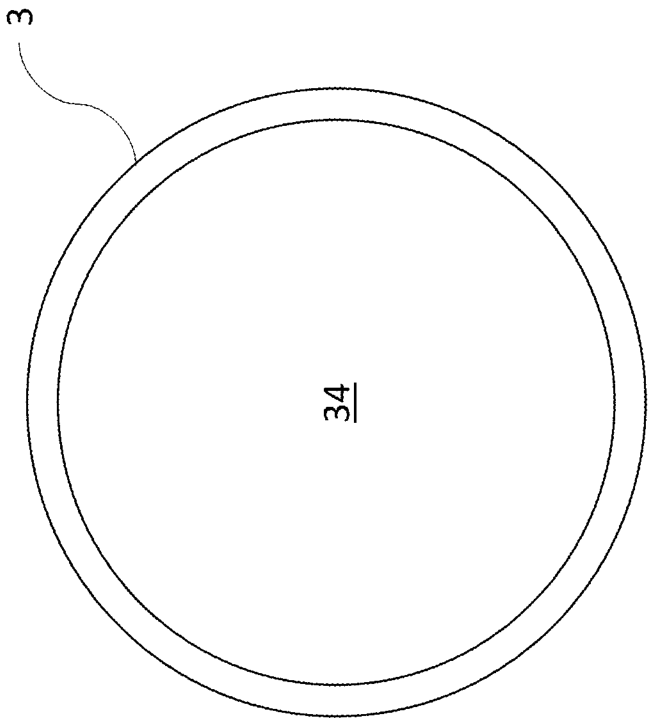
FIG. 5 is a schematic illustration of a cross-sectional view of the housing.

FIG. 5 shows a schematic illustration of a cross-section of the housing 3, disclosing the channel 34 as an open channel between the first opening 31 (shown in FIGS. 3, 4, 6) and the second opening 32 (shown in FIGS. 3, 4, 6, 12).

Figure 6:
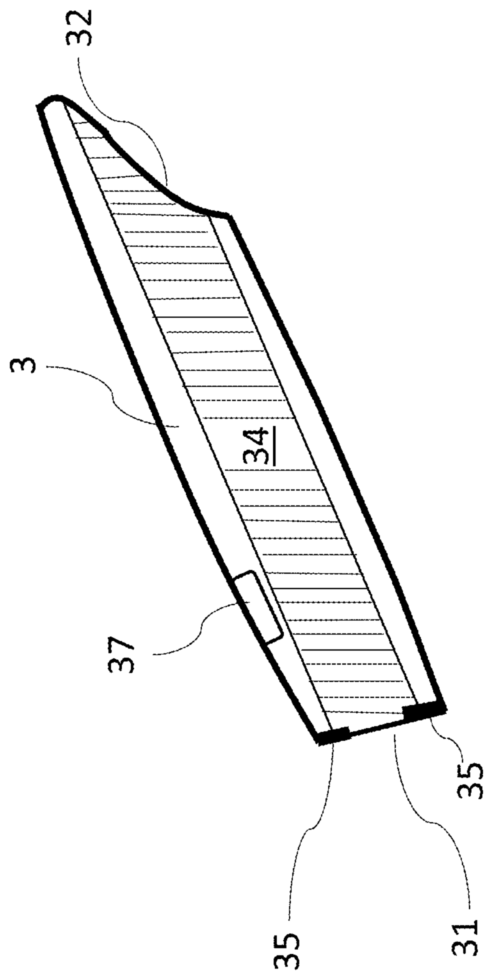
FIG. 6 is a schematic illustration of a cross-sectional view of the housing through a longitudinal axis of the housing.

FIG. 6 shows a schematic illustration of a cross-section of the housing 3 through the longitudinal direction of the housing 3, disclosing an inner surface of the channel 34, indicated by a shaded area between the first opening 31 and the second opening 32, the indication of the position 37 of a user interface as being a section that has been molded or formed together with the housing 3, and the flange 35 forming a 90 degree angled circular wall relative to an end portion of the housing 3 arranged at the first opening 31.

Figure 7:
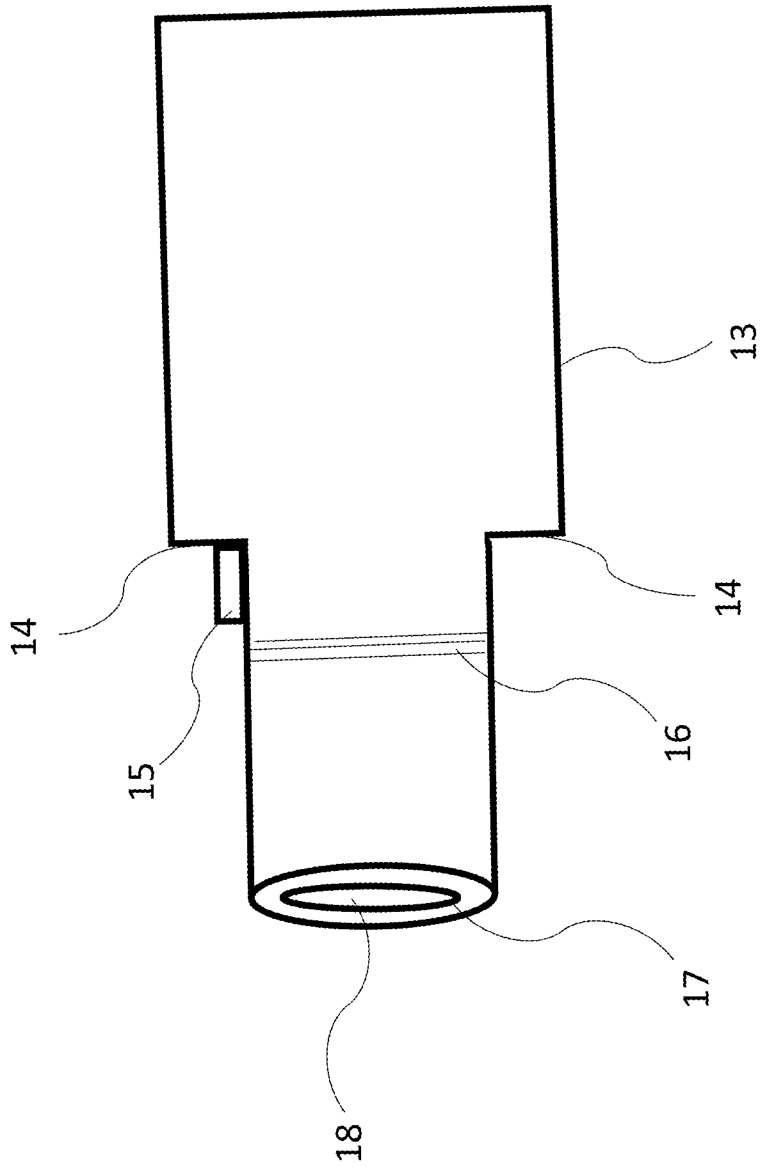
FIG. 7 is a schematic illustration of the support portion of the scan module.

FIG. 7 shows a schematic illustration of the support portion 13 of the scan module 1 (shown in FIG. 3) as being a frame. The support portion 13 has a portion that is configured to be arranged within the housing 3 (shown in FIG. 3) whereon parts of the scan module 1 are arranged, and a portion protruding out of the first opening 31 (shown in FIGS. 3, 4, 6) of the housing 3, whereon the connection element 4 (shown in FIGS. 3, 12, 13) and the retainer element 46 (shown in FIG. 3) are arranged. A portion of the scan module 1 is further configured to be inserted into a passage 24 (shown in FIG. 13) inside the scan tip 2 (shown in FIGS. 2, 3, 13). The support portion 13 is shown comprising an abutment 14 for abutting the flange 35 (shown in FIGS. 3, 4, 6) of the housing 3 and preventing the scan module 1 from sliding out of the first opening 31. The support portion 13 is shown comprising a protrusion 15 for being inserted into the groove 43 (shown in FIGS. 3, 8, 10) in the inner surface of the connection element 4 for preventing the connection element 4 from rotating. The support portion 13 is shown comprising a cylindrical portion comprising a channel 18 for allowing light to pass from the light emitter arranged on the scan module 1 into the passage 24 of the scan tip 2 and towards the dental object to be scanned inside the oral cavity.

Figure 8:
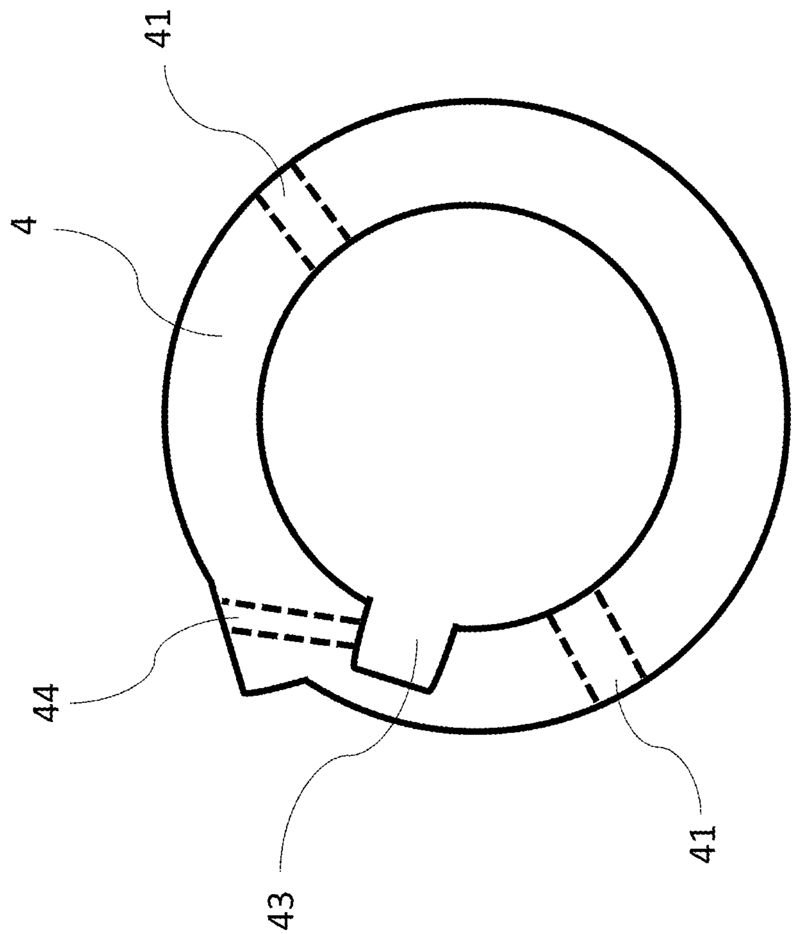
FIG. 8 is a schematic illustration of the connection element being a ring according to an embodiment of the disclosure.

FIG. 8 shows a front view of a schematic illustration of the connection element 4. The connection element 4 is shown as a ring having an outer surface and an inner surface. The outer surface comprises two holes 41 for receiving a screw 42 (shown in FIGS. 2 and 3) in each, for connecting the connection element 4 with the scan tip 2 (shown in FIGS. 2, 3, 13). The connection occurs, when the holes 22 (shown in FIG. 3) in the side wall of the scan tip 2 are aligned with the holes 41 in the side wall of the connection element 4, and a screw 42 is inserted in each hole 22, 41, thereby connecting the connection element 4 to the scan tip 2.

The connection element 4 further comprises a groove 43 for accommodating the protrusion 15 (shown in FIGS. 3, 7, 10) of the support portion 13 (shown in FIGS. 3, 7, 12, 13) of the scan module 1 (shown in FIG. 3). An insertion element 45 (shown in FIG. 3), such as a screw, is inserted into an insertion hole 44 through the surface of the connection element 4 for preventing a rotation of the connection element 4 around an axis along the longitudinal direction of the scan module 1.

Figure 9:
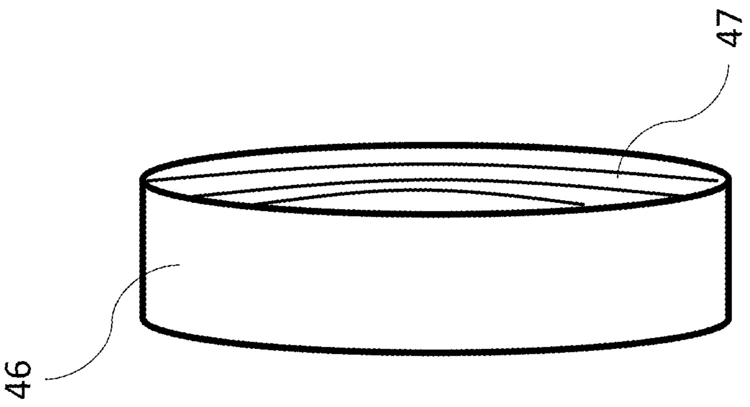
FIG. 9 is a schematic illustration of the retainer element being a ring according to an embodiment of the disclosure.

FIG. 9 shows a schematic illustration of the retainer element 46 shown as a locking ring comprising a threaded portion 47 on the inner surface of the retainer element 46 for engagement with a threaded portion 16 (shown in FIGS. 7 and 10) on the outer surface of the support portion 13 (shown in FIGS. 3, 7, 12, 13) of the scan module 1 (shown in FIG. 3).

Figure 10B:
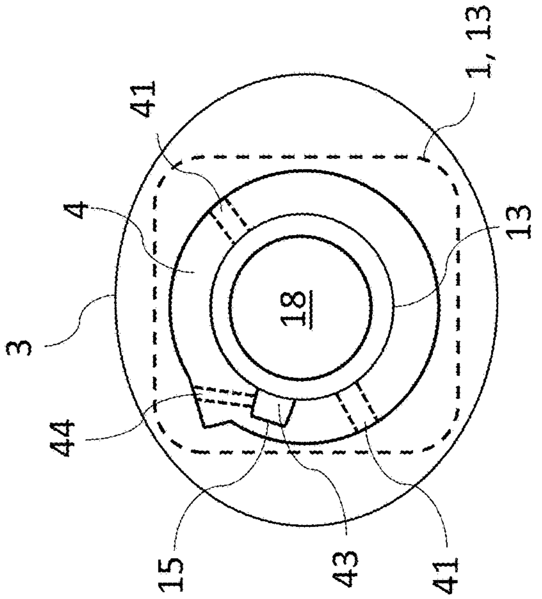
FIG. 10B is a schematic illustration of a front view of the illustration in FIG. 10A.
Figure 10A:
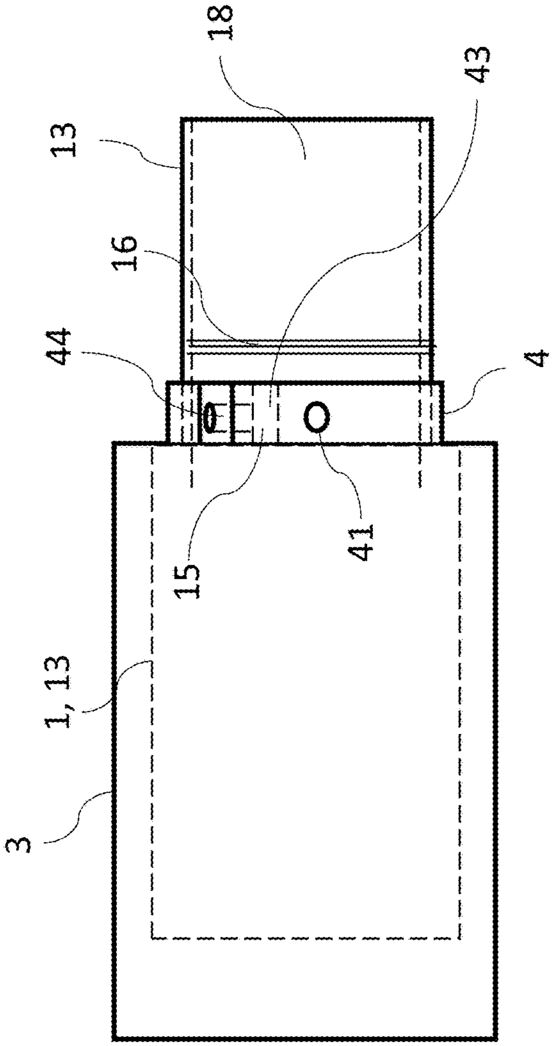
FIG. 10A is a schematic illustration of the connection element arranged on the support portion of the scan module and the scan module arranged inside the housing.

FIG. 10A shows a side view of a schematic illustration of the connection element 4 arranged on the support portion 13 of the scan module 1, and wherein the protrusion 15 of the support portion 13 is accommodated inside the groove 43 of the connection element 4.

FIG. 10B shows a front view of a schematic illustration of the figure in FIG. 10A. The protrusion 15 is shown accommodated inside the groove 43 of the support portion 13 of the scan module 1. The channel 18 through the scan module is further shown as a having a circular cross-section. A portion of the scan module 1 is shown (by a dotted square) accommodated inside the housing 3.

Figure 11:
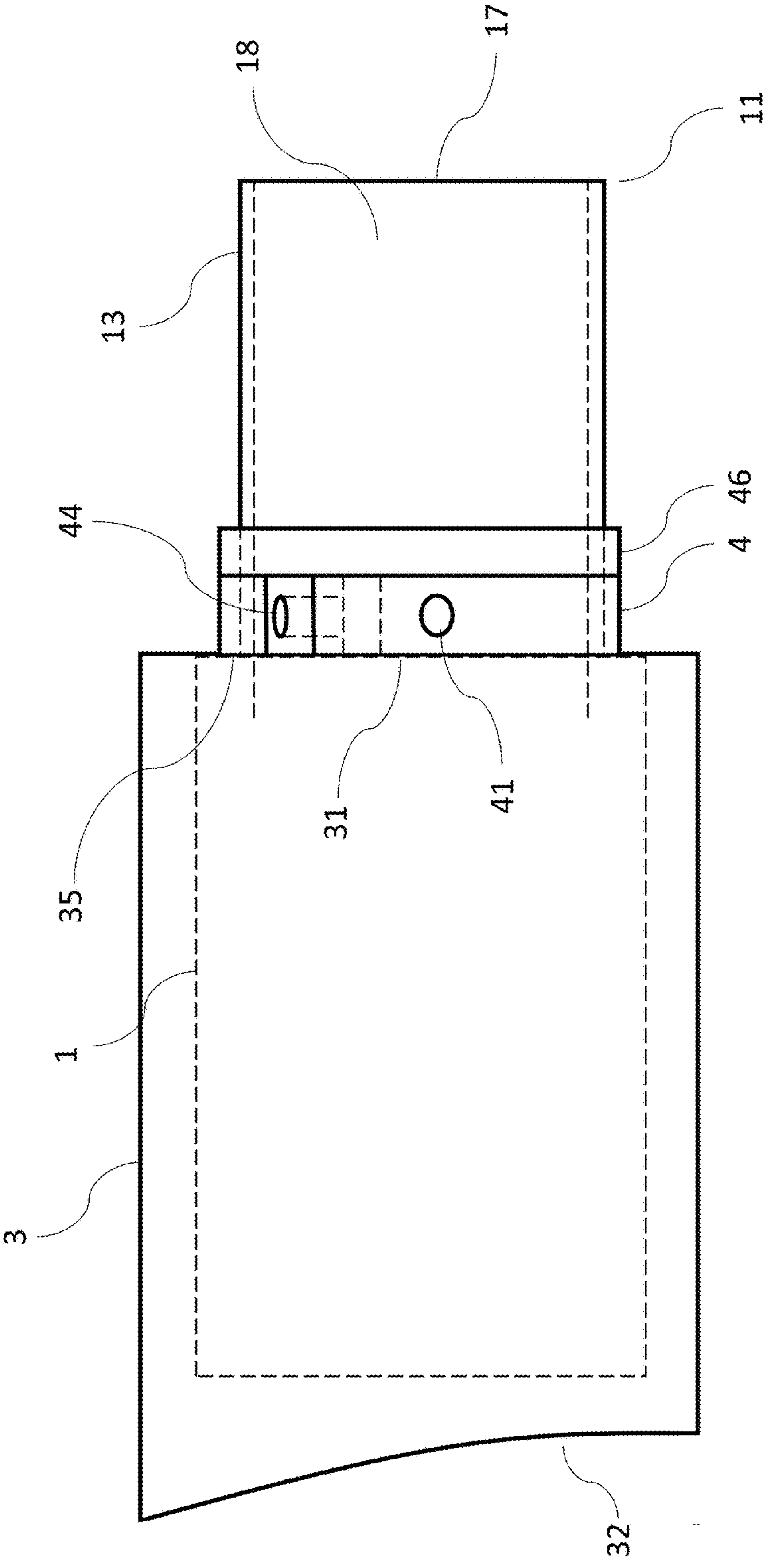
FIG. 11 is a schematic illustration of the support portion of the scan module arranged in the housing.

FIG. 11 shows a schematic illustration of the support portion 13 of the scan module 1 protruding out of the first opening 31 of the housing 3, and showing the retainer element 46 arranged on the support portion 13 of the scan module 1. The retainer element 46 is shown abutting the connection element 4, thereby pressing the connection element 4 against one side of the flange 35 (shown in more details in FIGS. 3, 4, 6) of the housing 3, thereby pressing the flange 35 against the abutment 14 (shown in FIG. 7) of the support portion 13 of the scan module 1 on the other side of the flange 35, thereby connecting the connection element 4 to the scan module 1 and preventing the scan module 1 from sliding out of the second opening 32 of the housing 3.

Figure 12:
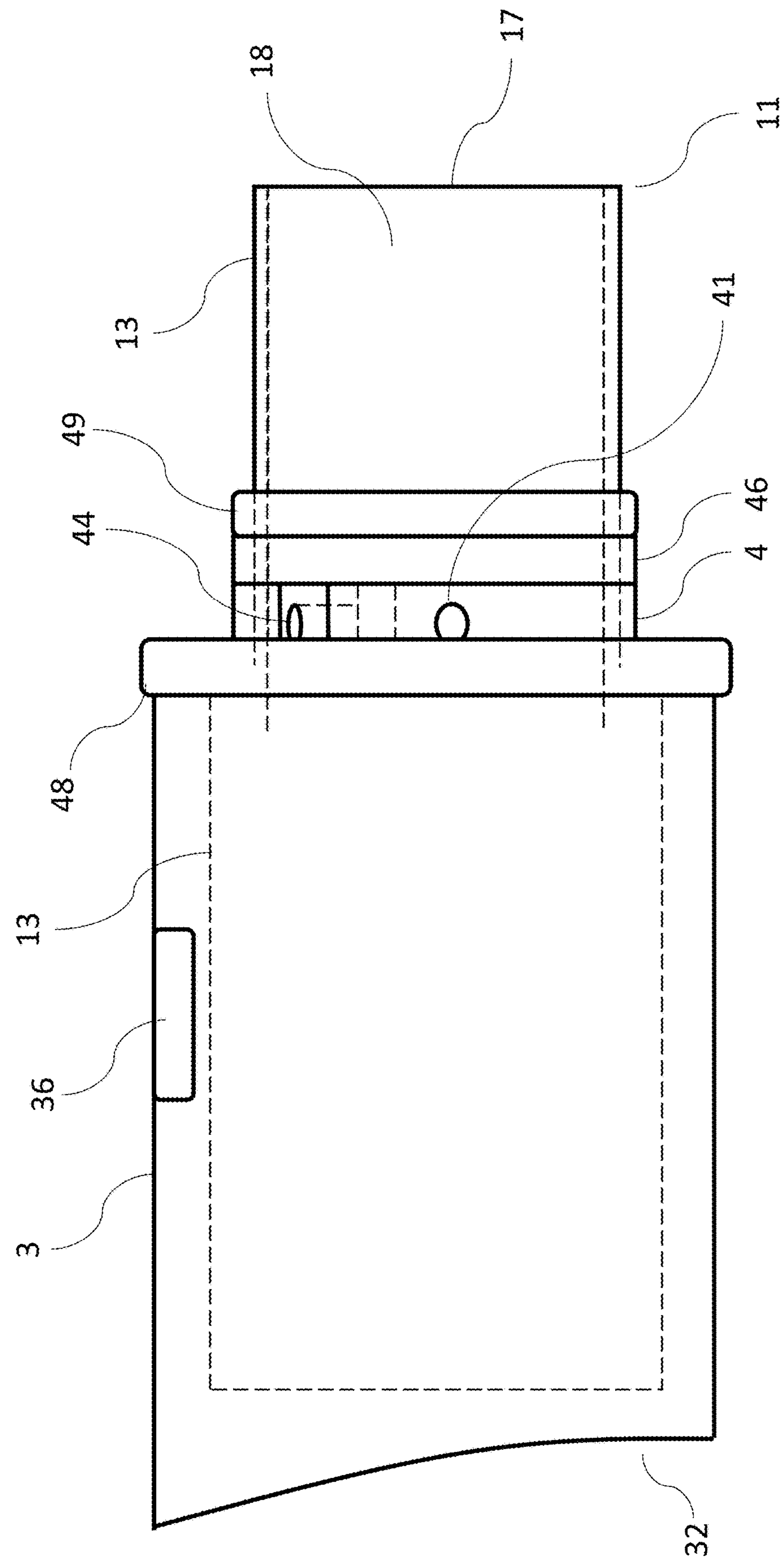
FIG. 12 is a schematic illustration of the sealing element arranged on the support portion of the scan module and on the housing.

FIG. 12 shows a schematic illustration of the support portion 13 protruding out of the first opening 31 of the housing 3, the connection element 4 arranged on the support portion 13, the retainer element 46 arranged on the support portion 13, the sealing element 48 arranged at an interface 39 (shown in FIG. 2 between the scan tip 2 (shown in FIGS. 2, 3, 13) (when connected) and the housing 3, and the protection element 49 arranged on the support portion 13 of the scan module 1 abutting the retainer element 46.

Figure 13:
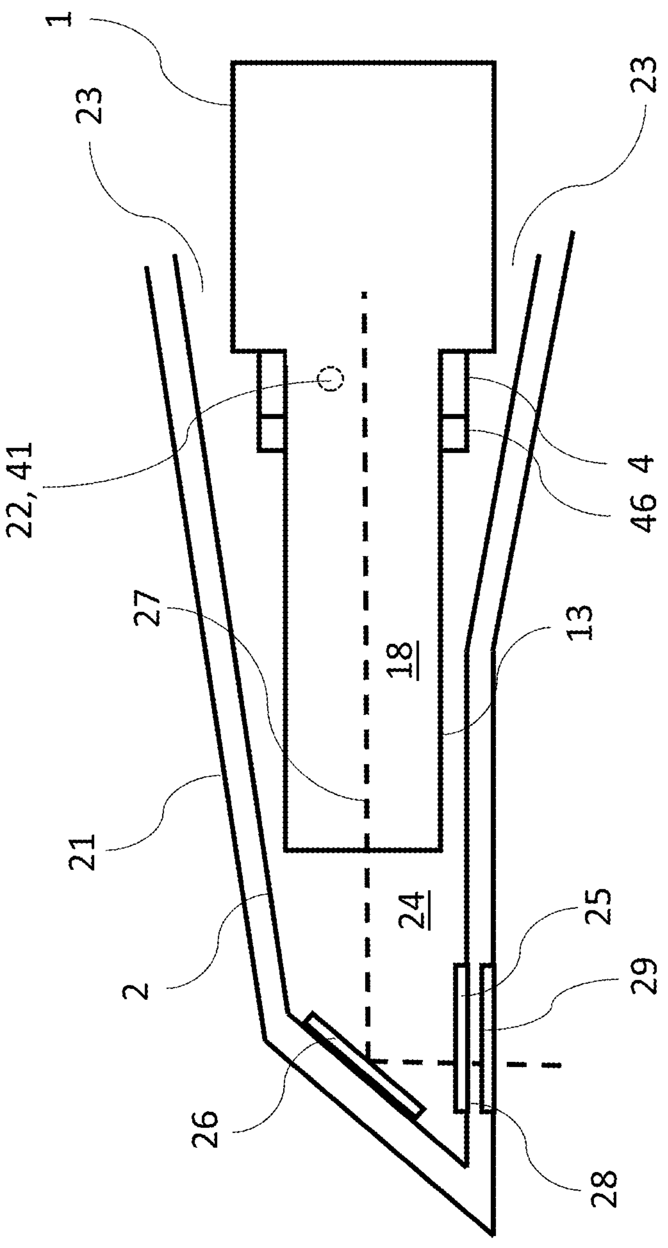
FIG. 13 is a schematic illustration of a cross-sectional view through a longitudinal axis of the handheld intraoral scanner.

FIG. 13 shows a schematic illustration of a cross-sectional view of the support portion 13 of the scan module 1 connected to the scan tip 2 and of the scan tip cover 21 and the cover window 29. The cross-sectional view of the scan tip 2 is shown disclosing the scan tip 2 comprising a passage 24 between a first opening 23 of the scan tip 2 and a second opening 28 of the scan tip 2. The second opening 28 of the scan tip 2 is covered by a window 25 for preventing fluids such as saliva and blood from a patient to enter the passage 24 and for allowing light to pass through. The scan tip 2 is further shown comprising a mirror 26 arranged at a 45 degrees angle relative to the passage 24 of the scan tip 2, and arranged at the second opening 28 covered by the window 25. An optical axis 27 is indicated by a dotted line. The optical axis 27 is defined between the light source inside the scan module 1 and the dental object in the oral cavity. The optical axis 27 goes through the channel 18 of the support portion 13 of the scan module 1, through the passage 24 of the scan tip 2, is reflected in a 45 degrees angle by the mirror 26, and goes through the window 25. A protruding portion of the support portion 13 of the scan module 1 is shown arranged inside the passage 24 of the scan tip 2 and connected to the scan tip 2 by a screw 42 (shown in FIG. 3) going through a hole 22 (position indicated by a dotted circle) through the wall of the scan tip 2 and a hole 41 (position indicated by a dotted circle) going through the wall of the connection element 4. The retainer element 46 is also disclosed abutting the connection element 4.

Although some embodiments have been described and shown in detail, the disclosure is not restricted to such details, but may also be embodied in other ways within the scope of the subject matter defined in the following claims. In particular, it is to be understood that other embodiments may be utilized, and structural and functional modifications may be made without departing from the scope of the present invention.

Benefits, other advantages, and solutions to problems have been described herein with regard to specific embodiments. However, the benefits, advantages, solutions to problems, and any component(s)/unit(s) that may cause any benefit, advantage, or solution to occur or become more pronounced are not to be construed as critical, required, or essential features or components/elements of any or all the claims or the invention. The scope of the invention is accordingly to be limited by nothing other than the appended claims, in which reference to an component/unit/element in the singular is not intended to mean "one and only one" unless explicitly so stated, but rather "one or more." A claim may refer to any of the preceding claims, and "any" is understood to mean "any one or more" of the preceding claims. It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. Furthermore, "connected" or "coupled" as used herein may include wirelessly connected or coupled. As used herein, the term "and/o"" includes any and all combinations of one or more of the associated listed items. The steps of any disclosed method is not limited to the exact order stated herein, unless expressly stated otherwise.

It should be appreciated that reference throughout this specification to "one embodiment" or ""an embodiment"" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Items

1. A handheld intraoral scanner configured to acquire intraoral scan data from a three-dimensional dental object during a scanning session, comprising:
   - a scan module that includes at least one active electronic component;
   - a scan tip configured to be connected to the scan module; and
   - a housing configured to enclose at least a part of the scan module, wherein the at least part of the scan module includes the at least active electronic components and that consists of a single piece and comprising a first opening and a second opening opposite to the first opening, wherein one or both of the first opening and second opening are configured to receive at least a part of the scan module.

1B. A handheld intraoral scanner configured to acquire intraoral scan data from a three-dimensional dental object during a scanning session, comprising:
   - a scan module;
   - a scan tip configured to be connected to the scan module; and
   - a housing configured to enclose at least a part of the scan module and that is made in a single piece and comprising a first opening and a second opening opposite to the first opening, wherein one or both of the first opening and second opening are configured to receive at least a part of the scan module.

1C. A handheld intraoral scanner configured to acquire intraoral scan data from a three-dimensional dental object during a scanning session, comprising:
   - a scan module;
   - a scan tip configured to be connected to the scan module; and
   - a housing configured to enclose at least a part of the scan module and that is made as a single piece and comprising a first opening and a second opening opposite to the first opening, wherein one or both of the first opening and second opening are configured to receive at least a part of the scan module.

2. A handheld intraoral scanner according to item 1, wherein the housing comprises an open channel defined between the first opening and the second opening, and wherein the channel is configured to accommodate the at least part of the scan module.

3. A handheld intraoral scanner according to any of the previous items, wherein at least a part of the scan module is configured to slide into either the first opening or the second opening of the housing.

4. A handheld intraoral scanner according to any of the previous items and item 2, wherein the open channel of the housing is configured to support a sliding motion of the scan module.

5. A handheld intraoral scanner according to any of the previous items, wherein at least a part of the scan module is configured to be slided into either the first opening or the second opening of the housing, and when the scan module is slided into one of the first opening or second opening of the housing, at least a part of the scan module is configured to protrude out of the first opening of the housing, when the scan module is in place in the housing.

6. A handheld intraoral scanner according to any of the previous items wherein the housing comprises a flange at the first opening configured to abut an abutment of the scan module.

7. A handheld intraoral scanner according to the previous item, wherein the flange is configured to prevent at least a part of the scan module from moving out of the first opening when a part of the scan module is received by the housing.

8. A handheld intraoral scanner according to the previous items 6-7, wherein the scan module comprises an abutment, configured to abut the flange of the housing.

9. A handheld intraoral scanner according to any of the previous items, wherein the scan module comprises a support portion arranged at a first end of the scan module and configured to be connected to a connection element or to the scan tip.

10. A handheld intraoral scanner according to any of the previous items, wherein the handheld intraoral scanner further comprises a connection element configured to connect the scan tip to the scan module or the scan tip to the support portion.

11. A handheld intraoral scanner according to the previous item, wherein:
   - the scan tip comprises one or more holes;
   - the connection element comprises one or more holes;

and wherein the one or more holes of the scan tip and the one or more holes of the connection element are configured to be aligned when the scan tip is connected to the scan module or to the support portion, and wherein each of the one or more holes of the scan tip and the one or more holes of the connection element is configured to receive a screw when the scan tip is connected to the connection element.

12. A handheld intraoral scanner according to any of the previous items 10-11, wherein the connection element is configured to be arranged on the support portion of the scan module.

13. A handheld intraoral scanner according to any of the previous items 10-12 and items 5, wherein the connection element is configured to be arranged on the part of the scan module that protrudes out of the first opening.

14. A handheld intraoral scanner according to any of the previous items 10-13, wherein a surface of the connection element comprises a groove configured to accommodate a protrusion of the scan module or of the support portion of the scan module.

15. A handheld intraoral scanner according to the previous item, wherein the scan module or the support portion comprises a protrusion that is configured to be accommodated by the groove in the surface of the connection element.
16. A handheld intraoral scanner according to any of the previous items 14-15, wherein the protrusion of the scan module or the support portion is configured to prevent a rotation of the connection element around an axis through the longitudinal direction of the connection element, when the protrusion is accommodated by the groove of the connection element.
17. A handheld intraoral scanner according to any of the items 10-16, wherein a retainer element is configured to be arranged on the scan module or on the support portion of the scan module and configured to retain a position of the connection element.
18. A handheld intraoral scanner according to any of the items 10-16, wherein a retainer element is configured to be arranged on the scan module or on the support portion of the scan module and configured to prevent a movement of the connection element.
19. A handheld intraoral scanner according to any of the previous items 10-18, wherein the connection element is a ring that is configured to connect the scan module to the scan tip.
20. A handheld intraoral scanner according to any of the previous items 18-19 wherein the retainer is a retainer ring or a nut.
21. A handheld intraoral scanner according to any of the previous items, wherein a sealing element is provided between the scan tip and the housing configured to prevent fluids from reaching an interface or entering a gap between the scan tip and the scan module.
22. A handheld intraoral scanner according to the previous item, wherein the sealing element is a gasket or an O-ring.
23. A handheld intraoral scanner according to any of the previous items, wherein:
    the scan module comprises an optical lens,
    the scan tip comprises a passage, configured to allow light to pass through at least a part of the passage, and wherein when the scan tip is connected to the scan module, an optical axis is defined between the optical lens and a cross-section of at least a part of the passage.
24. A handheld intraoral scanner according to any of the previous items 10-23, wherein:
    the scan module comprises an optical lens,
    the scan tip comprises a passage, configured to allow light to pass through at least a part of the passage, and wherein when the scan tip is connected to the scan module, an optical axis between the optical lens and the scan tip passes through a cross-section of the connection element.
25. A handheld intraoral scanner according to any of the previous items, wherein the scan tip is configured to be aligned with the scan module by connecting the scan tip to an outer surface of the ring and connecting the scan module to an inner surface of the ring, or vice versa.
26. A handheld intraoral scanner according to any of the previous items 10-25, wherein the scan module is configured to be aligned with the connection element, and wherein the scan tip is configured to be aligned with the connection element.
27. A handheld intraoral scanner according to any of the previous items, wherein the housing comprises a user interface or an indication of a position of a user interface.
28. A handheld intraoral scanner according to any of the previous items, wherein the user interface or the indication of a position of a user interface comprises one or more buttons.
29. A handheld intraoral scanner according to any of the previous items, wherein the scan module comprises a support portion comprising a frame that is configured to support the scan module or the parts of the scan module, and wherein the frame is configured to be connected to a connection element or to the scan tip.
30. A handheld intraoral scanner according to any of the previous claims, wherein the at least one active electronic components comprises at least one of a processor unit, a central processor unit, a graphics processor unit, a drive unit, and/or an electric motor.

The invention claimed is:

1. A handheld intraoral scanner configured to acquire intraoral scan data from a three-dimensional dental object during a scanning session, comprising:
    a scan module that includes at least one active electronic component;
    a scan tip configured to be connected to the scan module; and
    a housing configured to enclose at least a part of the scan module, wherein the at least part of the scan module includes the at least one active electronic components, and wherein the housing consists of a single piece and comprising a first opening and a second opening opposite to the first opening, wherein one or both of the first opening and second opening are configured to receive at least a part of the scan module;

wherein the scan module comprises a frame housing that accommodates the at least one active electronic components, and wherein the frame housing includes a support portion that is configured to support the frame housing to the housing, and wherein the support portion is arranged outside the housing and the remaining of the frame housing is arranged within the housing and wherein a connection element is removably fixated to the support portion and an outer surface of the housing; and wherein a protrusion of the scan module is configured to prevent a rotation of the connection element around an axis in a longitudinal direction of the connection element, when the protrusion abuts a groove of the connection element.

2. A handheld intraoral scanner according to claim 1, wherein the housing comprises an open channel defined between the first opening and the second opening, and wherein the channel is configured to accommodate the at least part of the scan module.

3. A handheld intraoral scanner according to claim 1, wherein;
    the housing comprises a flange at the first opening configured to abut an abutment of the scan module,
    the scan module comprises an abutment configured to abut the flange of the housing, and wherein the flange is configured to prevent at least a part of the scan module from moving out of the first opening when a part of the scan module is received by the housing.

4. A handheld intraoral scanner according to claim 1, wherein at least a part of the scan module is configured to be slided into either the first opening or the second opening of the housing, and when the scan module is slided into one of the first opening or second opening of the housing, at least a part of the scan module is configured to protrude out of the first opening of the housing, when the scan module is in place in the housing.

5. The handheld intraoral scanner according to claim 1, wherein the connection element is removably fixated to the support portion and a flange of the outer surface of the housing.

6. A handheld intraoral scanner according to claim 1, wherein the protrusion of the scan module is arranged on an outer surface of the support portion.

7. A handheld intraoral scanner configured to acquire intraoral scan data from a three-dimensional dental object during a scanning session, comprising:

a scan module that includes at least one active electronic component;

a scan tip configured to be connected to the scan module; and a housing configured to enclose at least a part of the scan module, wherein the at least part of the scan module includes the at least one active electronic components, and wherein the housing consists of a single piece and comprising a first opening and a second opening opposite to the first opening, wherein one or both of the first opening and second opening are configured to receive at least a part of the scan module; wherein the scan module comprises a frame housing that accommodates the at least one active electronic components, and wherein the frame housing includes a support portion that is configured to support the frame housing to the housing, and wherein the support portion is arranged outside the housing and the remaining of the frame housing is arranged within the housing and wherein a connection element is removably fixated to the support portion and an outer surface of the housing; and wherein a protrusion of the scan module is configured to prevent a rotation of the connection element around an axis in a longitudinal direction of the connection element, when the protrusion abuts a groove of the connection element; and wherein the scan tip includes one or more holes, and the connection element comprises one or more holes, and wherein the one or more holes of the scan tip and the one or more holes of the connection element are configured to be aligned when the scan tip is connected to the scan module or to the support portion, and wherein a screw is configured to be inserted through each of the one or more holes of the scan tip and the one or more holes of the connection element when the scan tip is connected to the connection element.

8. A handheld intraoral scanner configured to acquire intraoral scan data from a three-dimensional dental object during a scanning session, comprising:

a scan module that includes at least one active electronic component;

a scan tip configured to be connected to the scan module; and a housing configured to enclose at least a part of the scan module, wherein the at least part of the scan module includes the at least one active electronic components, and wherein the housing consists of a single piece and comprising a first opening and a second opening opposite to the first opening, wherein one or both of the first opening and second opening are configured to receive at least a part of the scan module;

wherein the scan module comprises a frame housing that accommodates the at least one active electronic components, and wherein the frame housing includes a support portion that is configured to support the frame housing to the housing, and wherein the support portion is arranged outside the housing and the remaining of the frame housing is arranged within the housing and wherein a connection element is removably fixated to the support portion and an outer surface of the housing; and wherein a protrusion of the scan module is configured to prevent a rotation of the connection element around an axis in a longitudinal direction of the connection element, when the protrusion abuts a groove of the connection element; and wherein the connection element is a ring that is configured to connect the scan module to the scan tip.

9. A handheld intraoral scanner according to claim 7, wherein:

the scan module comprises an optical lens, the scan tip comprises a passage, configured to allow light to pass through at least a part of the passage, and wherein when the scan tip is connected to the scan module, an optical axis between the optical lens and the scan tip passes through a cross-section of the connection element.

10. A handheld intraoral scanner according to claim 8, wherein the scan tip is configured to be aligned with the scan module by connecting the scan tip to an outer surface of the ring and connecting the scan module to an inner surface of the ring, or vice versa.

11. A handheld intraoral scanner according to claim 1, wherein the at least one active electronic components comprises at least one of a processor unit, a central processor unit, a graphics processor unit, a drive unit, and/or an electric motor.

12. A handheld intraoral scanner according to claim 1, wherein a sealing element is provided between the scan tip and the housing, and configured to prevent fluids from reaching an interface or entering a gap between the scan tip and the scan module.

* * * * *